(12) United States Patent
Ma (10) Patent No.: US 12,171,970 B2
(45) Date of Patent: Dec. 24, 2024

(54) CATHETER ASSEMBLY WITH DIRECTIONAL PORT OPENING

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 120 days.

(21) Appl. No.: 17/490,989

(22) Filed: Sep. 30, 2021

(65) Prior Publication Data
US 2022/0111191 A1    Apr. 14, 2022

Related U.S. Application Data

(60) Provisional application No. 63/090,585, filed on Oct. 12, 2020.

(51) Int. Cl.
*A61M 39/02* (2006.01)
*A61M 5/145* (2006.01)
(Continued)

(52) U.S. Cl.
CPC ...... *A61M 39/0247* (2013.01); *A61M 5/1452* (2013.01); *A61M 25/0097* (2013.01);
(Continued)

(58) Field of Classification Search
CPC ...... A61M 25/0097; A61M 2039/0258; A61M 2039/0264; A61M 25/0606; A61M 39/0247; A61M 39/0606; A61M 2039/0633; A61M 2039/027; A61M 39/22; A61M 39/26; A61M 39/06; A61M 2039/266; A61M 2039/066; A61M 2039/1072; A61M 2039/2493;
(Continued)

(56) References Cited

U.S. PATENT DOCUMENTS 4,983,162 A * 1/1991 Metais ............... A61M 39/0247
6,808,161 B1 * 10/2004 Hishikawa ............ A61M 39/26
(Continued)

FOREIGN PATENT DOCUMENTS

AU    2015209607 A1    8/2016
AU    2015209608 A1    8/2016
(Continued)

*Primary Examiner* — Lauren P Farrar
*Assistant Examiner* — Kathleen Paige Farrell
(74) *Attorney, Agent, or Firm* — Kirton McConkie; Whitney Blair; Kevin Stinger (57) ABSTRACT

A vascular access device including a catheter adapter, a port opening, and an elastomeric valve. The catheter adapter extends along a longitudinal axis and includes a proximal end, a distal end, and a lumen extending therebetween. The port opening is formed in a surface of the catheter adapter in fluid communication with a side port of the catheter adapter and the lumen. A structural geometry of the port opening directs a fluid into the lumen in a proximal direction. The elastomeric port valve is disposed within the lumen and configured to deform in response to a transverse force applied thereto. A proximal gap may result between the inner wall forming the lumen and a proximal side of the elastomeric port valve, thereby opening a fluid path.

7 Claims, 5 Drawing Sheets

(51) Int. Cl.
*A61M 25/00* (2006.01)
*A61M 39/06* (2006.01)

(52) U.S. Cl.
CPC . *A61M 39/0606* (2013.01); *A61M 2039/0258* (2013.01); *A61M 2039/0264* (2013.01); *A61M 2039/0282* (2013.01); *A61M 2039/0633* (2013.01)

(58) Field of Classification Search
CPC .......... A61M 2039/064; A61M 5/1452; A61M 2039/0282; A61M 39/10; A61M 2039/12; A61M 39/02; A61M 2039/1077; A61M 39/00
See application file for complete search history.

(56) References Cited

U.S. PATENT DOCUMENTS

| | | | |
|---|---|---|---|
| 2013/0090607 | A1 | 4/2013 | McKinnon et al. |
| 2015/0202421 | A1 | 7/2015 | Ma et al. |
| 2015/0202422 | A1* | 7/2015 | Ma et al. ............. A61M 39/00 |
| 2016/0008569 | A1 | 1/2016 | Harding |
| 2016/0089529 | A1* | 3/2016 | Bolz et al. ............. A61M 39/10 |
| 2016/0361529 | A1* | 12/2016 | Finch, Jr. ............. A61M 1/3659 |
| 2017/0348518 | A1 | 12/2017 | Ma et al. |
| 2017/0361070 | A1 | 12/2017 | Hivert |
| 2018/0140820 | A1 | 5/2018 | Ma et al. |
| 2018/0304041 | A1* | 10/2018 | Leeflang ........... A61M 39/0606 |
| 2019/0091462 | A1* | 3/2019 | Bihlmaier et al. .... A61M 39/00 |
| 2019/0314602 | A1 | 10/2019 | Harding |
| 2020/0121896 | A1* | 4/2020 | Baid ..................... A61M 39/06 |
| 2020/0222662 | A1 | 7/2020 | Naidu et al. |

FOREIGN PATENT DOCUMENTS

| | | |
|---|---|---|
| AU | 2015288076 A1 | 2/2017 |
| AU | 2012318627 B2 | 3/2017 |
| AU | 2015373377 A1 | 7/2017 |
| AU | 2018278990 A1 | 1/2019 |
| AU | 2020208143 A1 | 7/2021 |
| BR | 112014008253 A2 | 4/2017 |
| BR | 112017000239 A2 | 10/2017 |
| BR | 112017014247 A1 | 2/2018 |
| BR | 112021013648 A2 | 9/2021 |
| CA | 2851233 A1 | 4/2013 |
| CA | 2937165 A1 | 7/2015 |
| CA | 2937166 A1 | 7/2015 |
| CA | 2954387 A1 | 1/2016 |
| CA | 2972544 A1 | 7/2016 |
| CA | 3125907 A1 | 7/2020 |
| CN | 202844311 U | 4/2013 |
| CN | 103957985 A | 7/2014 |
| CN | 204684328 U | 10/2015 |
| CN | 204723492 U | 10/2015 |
| CN | 204951703 U | 1/2016 |
| CN | 106029152 A | 10/2016 |
| CN | 106061539 A | 10/2016 |
| CN | 106345038 A | 1/2017 |
| CN | 106659867 A | 5/2017 |
| CN | 107106817 A | 8/2017 |
| CN | 110074792 A | 8/2019 |
| CN | 111228628 A | 6/2020 |
| CN | 212090487 U | 12/2020 |
| EP | 2763738 A1 | 8/2014 |
| EP | 3096828 A1 | 11/2016 |
| EP | 3096829 A1 | 11/2016 |
| EP | 3120894 A1 | 1/2017 |
| EP | 3166681 A1 | 5/2017 |
| EP | 3240601 A1 | 11/2017 |
| EP | 3427785 A1 | 1/2019 |
| EP | 3911394 A2 | 11/2021 |
| ES | 2618018 T3 | 6/2017 |
| ES | 2665289 T3 | 4/2018 |
| ES | 2688049 T3 | 10/2018 |
| ES | 2708204 T3 | 4/2019 |
| ES | 2716414 T3 | 6/2019 |
| ES | 2845182 T3 | 7/2021 |
| JP | 2014528330 A | 10/2014 |
| JP | 2017503598 A | 2/2017 |
| JP | 2017503599 A | 2/2017 |
| JP | 2017520341 A | 7/2017 |
| JP | 6272760 B2 | 1/2018 |
| JP | 2018047371 A | 3/2018 |
| JP | 2018505713 A | 3/2018 |
| JP | 6483713 B2 | 3/2019 |
| JP | 2019051353 A | 4/2019 |
| JP | 6535017 B2 | 6/2019 |
| JP | 6603340 B2 | 11/2019 |
| JP | 6608909 B2 | 11/2019 |
| JP | 2021006257 A | 1/2021 |
| JP | 6942109 B2 | 9/2021 |
| KR | 20170102918 A | 9/2017 |
| KR | 20210116524 A | 9/2021 |
| MX | 343827 B | 11/2016 |
| MX | 367828 B | 9/2019 |
| SG | 11201605779 S | 8/2016 |
| SG | 11201605783 P | 8/2016 |
| SG | 11201610851 W | 1/2017 |
| SG | 10201900985 P | 3/2019 |
| SG | 11202107464 T | 8/2021 |
| WO | 2013052661 A1 | 4/2013 |
| WO | 2015112426 A1 | 7/2015 |
| WO | 2015112427 A1 | 7/2015 |
| WO | 2016/007440 | 1/2016 |
| WO | 2016/107922 | 7/2016 |
| WO | 2020150027 A2 | 7/2020 |

* cited by examiner

CATHETER ASSEMBLY WITH DIRECTIONAL PORT OPENING

RELATED APPLICATIONS

This application claims benefit of U.S. Provisional Patent Application No. 63/090,585, filed on Oct. 12, 2020, entitled CATHETER ASSEMBLY WITH DIRECTIONAL PORT OPENING, which is incorporated herein in its entirety.

BACKGROUND

In medicine, catheter assemblies are used to place a catheter properly into the vascular system of a patient. Once in place, catheters such as intravenous or "IV" catheters may be used to infuse fluids including normal saline, medicinal compounds, and/or nutritional compositions into a patient in need of such treatment. Catheters additionally enable the removal of fluids from the circulatory systems and monitoring of conditions within the vascular system of the patient.

One type of commonly used catheter is an over-the-needle catheter. As its name implies, a catheter that is "over-the-needle" may be mounted over an introducer needle having a sharp distal tip. The introducer needle typically has a sharp distal tip to pierce skin and the vein of the patient with minimal resistance to minimize the pain to the patient. Although several techniques for placing catheters are practiced in the art, many generally include the step of inserting at least a portion of the introducer needle into the target vessel and then sliding the catheter over the needle into place. Once placement of the introducer needle within the vein has been confirmed, the user may temporarily occlude flow in the vein and withdraw the introducer needle, leaving the catheter in place for future fluid infusion and/or blood withdrawal.

In some catheter assemblies, the catheter extends from a distal end of a catheter adapter. A side port of the catheter adapter may be used to administer fluid and medications through the catheter. A port valve may separate the side port from the primary fluid path. In some cases, the port valve may be deformed to allow the fluid and/or medications to enter. Such deformation, however, is difficult to reliably control and may inadvertently unseal the port opening, causing leakage of infusates or blood.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a vascular access device, as well as related devices, systems, and methods. In some embodiments, the vascular access device may include a catheter adapter extending along a longitudinal axis. Some embodiments of the catheter adapter may include a proximal end, a distal end, and a lumen extending therebetween.

In some embodiments, a port opening may be formed in a surface of the catheter adapter in fluid communication with a side port of the catheter adapter and the lumen. In some embodiments, the port opening may include a structural geometry to direct a fluid into the lumen in a proximal direction.

In some embodiments, an elastomeric port valve may be disposed within the lumen and may seal the port opening. Some embodiments of the elastomeric port valve may be configured to deform in response to a transverse force applied thereto. In some embodiments, deforming the elastomeric port valve may create a proximal gap between an inner wall forming the lumen and a proximal side of the elastomeric port valve to open a fluid path.

In some embodiments, the structural geometry may include a sloped surface to direct the fluid into the lumen in the proximal direction. In some embodiments, the sloped surface may extend in the proximal direction from a distal wall of the side port to the port opening. Some embodiments of the sloped surface may extend in a transverse direction from a position on the distal wall that is elevated relative to the port opening along a transverse axis, to a location adjacent to the port opening. In some embodiments, the port opening may be configured to couple to a syringe to deliver the fluid to the fluid path.

In some embodiments, the structural geometry may include a half-circle shape or a pie shape. In some embodiments, the structural geometry may include a rib extending across at least a portion of the port opening and oriented to direct the fluid in the proximal direction through the port opening.

In some embodiments, the port opening may be disposed proximate to a proximal wall of the side port. In some embodiments, the port opening may include a periphery smaller than a periphery of a distal end of the side port. In this manner, in some embodiments, the port opening may include a closed portion and an open portion.

Some embodiments of a method may include coupling an infusion device to a side port of a vascular access device. In some embodiments, the vascular access device may include the catheter adapter extending along the longitudinal axis and comprising the proximal end, the distal end, and the lumen extending therebetween. In some embodiments, a catheter may extend distally from the distal end of the catheter adapter.

In these and other embodiments, the side port may extend from the surface of the catheter adapter in a direction substantially transverse to the longitudinal axis. Some embodiments of the side port may communicate with the lumen through the port opening. In some embodiments, the port opening may include a structural geometry configured to direct the fluid into the lumen in the proximal direction. Some embodiments may further include an elastomeric port valve disposed within the lumen and sealing the port opening. In some embodiments, the elastomeric port valve may be secured within the lumen via friction. In some embodiments, the elastomeric port valve may be configured to deform in response to a force applied thereto.

In some embodiments, the method may further include activating the infusion device. In some embodiments, in response to activating the infusion device, a proximal end of the elastomeric port valve may be deformed and a proximal gap created between the proximal end of the elastomeric port valve and an inner surface of the catheter adapter. In this manner, some embodiments may create a fluid path such that fluid flows proximally through the elastomeric port valve and lumen.

In some embodiments, in response to activating the infusion device, a transverse force is applied to the elastomeric port valve via the infusion device to create the proximal gap. In some embodiments, coupling the infusion device to the side port may include inserting a syringe into the side port such that a distal end of the syringe is disposed adjacent to the port opening. In some embodiments, applying the transverse force may include depressing a plunger of the syringe to deform the elastomeric port valve. In some embodiments, depressing the plunger may force fluid from the distal end of the syringe to deform a side of the elastomeric port valve.

In some embodiments, in response to activating the infusion device, fluid may be directed through the structural geometry of the port opening. Some embodiments of the structural geometry may include a half-circle shape, a pie shape, or a circle shape having a circumference smaller than the distal end of the side port. In some embodiments, in response to activating the infusion device, fluid may be directed towards a rib disposed across the port opening. Some embodiments of the rib may include a contour to direct the fluid into the lumen in the proximal direction.

In some embodiments, in response to activating the infusion device, fluid may be directed towards a sloped surface. Some embodiments of the sloped surface may extend in the transverse direction from a distal wall of the side port to the port opening. In some embodiments, the sloped surface comprises an angle between about 30° and about 80°. In some embodiments, the sloped surface may include a curve.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
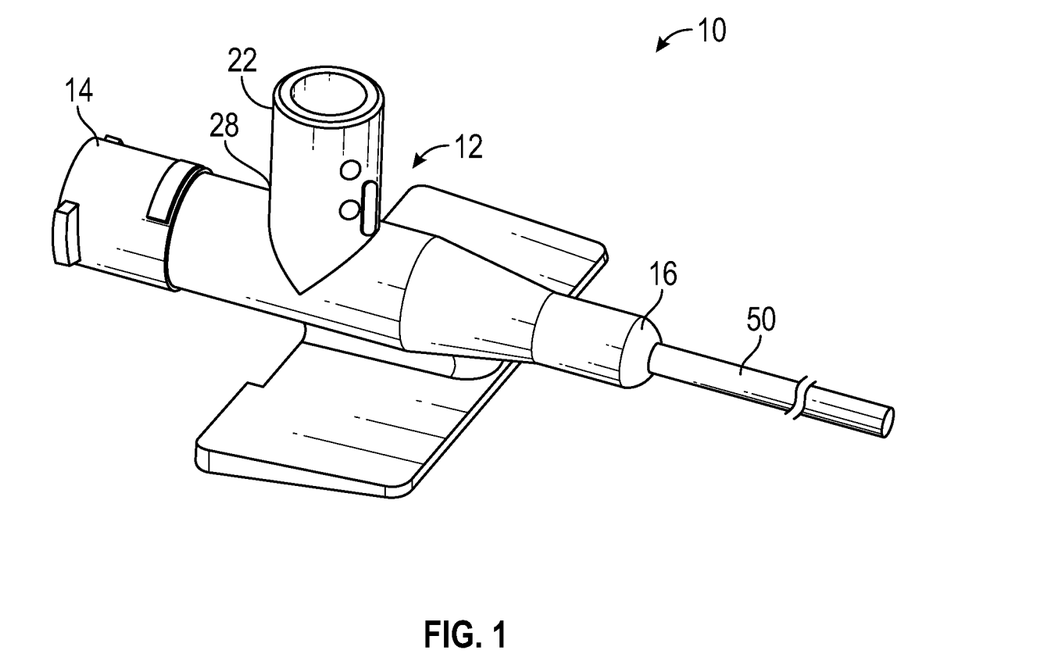
FIG. 1 is a perspective view of a catheter adapter, according to some embodiments.

Referring now to FIG. 1, as discussed above, a catheter adapter 12 may be used to administer fluid and medications through a catheter. In some embodiments, the catheter adapter 12 may include a side port 22 for introducing fluids and medications into the catheter adapter 12. In some embodiments, the side port 22 may extend from a port opening 28. Some embodiments of the side port 22 may be configured to direct the fluid into the port opening 28. In some embodiments, the port opening 28 may be disposed proximate to a proximal wall of the side port 22. In some embodiments, the port opening 28 may include reduced dimensions relative to the dimensions of a distal end 48 of the side port 22.

In some embodiments, the side port 22 may extend from a surface 52 of the catheter adapter 12 in a direction substantially transverse to a longitudinal axis 20. Some embodiments of the side port 22 may communicate with the lumen 18 through the port opening 28. In some embodiments, the port opening 28 may include a structural geometry configured to direct the fluid in the proximal direction as it enters the lumen 18 of the catheter adapter 12.

Figure 2:
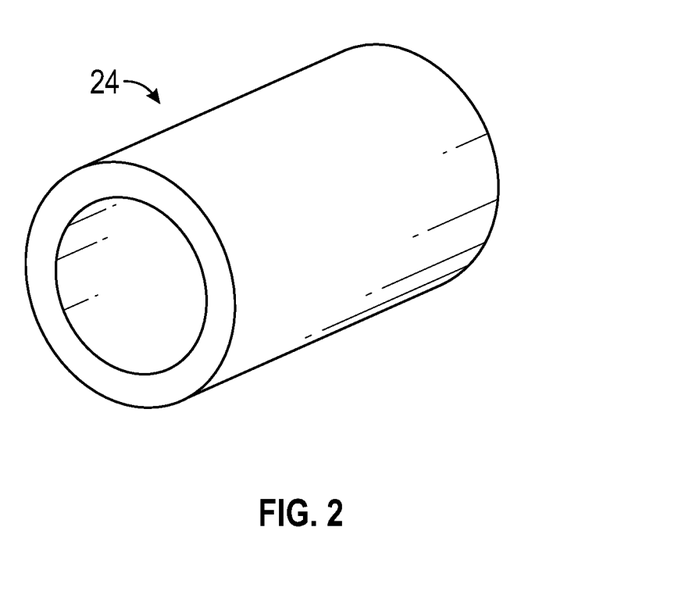
FIG. 2 is a perspective view of an elastomeric port valve, according to some embodiments.
Figure 3:
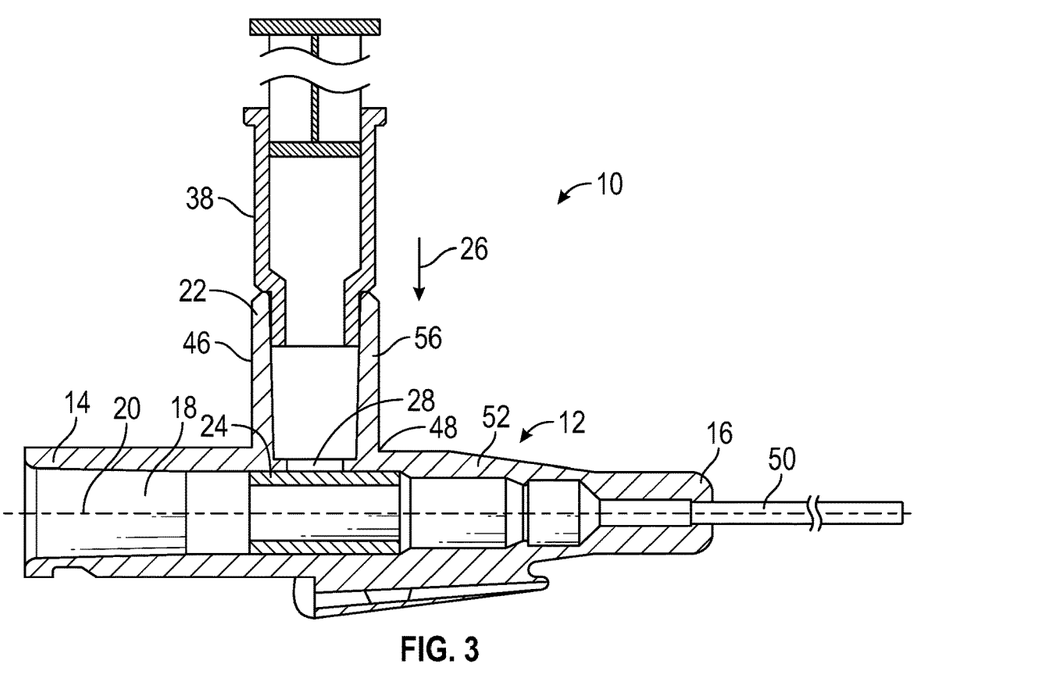
FIG. 3 is a cross-sectional view of a vascular access device, according to some embodiments.

As shown in FIGS. 2 and 3, a port valve 24 may separate the side port 22 from a primary fluid path through the port opening 28. In some cases, the port valve 24 may include a hollow shape formed from an elastomeric material such as rubber, for example. In this manner, some embodiments of the port valve 24 may deform to provide a fluid path for the fluid and/or medications to flow from the side port 22 into the lumen 18.

In some embodiments, the port valve 24 may be tubular. In some embodiments, the port valve 24 may be secured within the lumen 18 via friction, an adhesive, or any other suitable method or device. In some embodiments, the port valve 24 may be elastomeric and configured to deform in response to a transverse force applied thereto. In this manner, in some embodiments, a proximal gap may be created between an inner wall forming the lumen and a proximal side of the elastomeric port valve, thereby opening a fluid path.

In some embodiments, the port opening 28 may be disposed near the proximal end 14 of the catheter adapter 12. In some embodiments, the port opening 28 may be configured to receive a distal end of a syringe 38. In some embodiments, a transverse force 26 may be applied to the elastomeric valve 24 via the syringe or other device.

For example, in a clinical setting, a clinician may connect the syringe to the side port 22. In some embodiments, the side port 22 may be located on top of the catheter adapter 12. In some embodiments, downward pressure generated by the clinician in pushing down on the plunger of the syringe may deform the elastomeric port valve 24, thereby creating a gap between the elastomeric port valve 24 and the catheter adapter 12.

In some embodiments, the gap between the elastomeric port valve 24 and the catheter adapter 12 may provide a fluid path between the side port 22 and the lumen 18. In some embodiments, this may enable fluid and/or medications to enter the catheter adapter 12 for administration through the catheter. In some cases, however, deformation of the elastomeric port valve 24 may inadvertently unseal the port opening 28, causing leakage of infusates or blood.

Referring now to FIG. 2, some embodiments of an elastomeric port valve 24 may include a tubular or cylindrical structure, or any other suitable structure configured to provide a fluid path therethrough. Some embodiments of the elastomeric port valve 24 may include outside dimensions substantially corresponding to inside dimensions of the lumen 18. In this manner, some embodiments of the elastomeric port valve 24 may be retained within the lumen 18 of the catheter adapter 12 by friction or a press fit.

Some embodiments of the elastomeric port valve 24 may be hollow or may include a channel to provide the fluid path. In some embodiments, the elastomeric port valve 24 may include a biocompatible elastomeric material such as rubber.

Referring now to FIG. 3, in some embodiments, a vascular access device 10 may include the catheter adapter 12 extending along the longitudinal axis 20. Some embodiments of the catheter adapter 12 may include a proximal end 14, a distal end 16, and a lumen 18 extending therebetween. In some embodiments, the port opening 28 may be formed in the surface 52 of the catheter adapter 12 at a location proximate to the proximal end 14 of the catheter adapter 12. The port opening 28 may be in fluid communication with the lumen 18.

Figure 4:
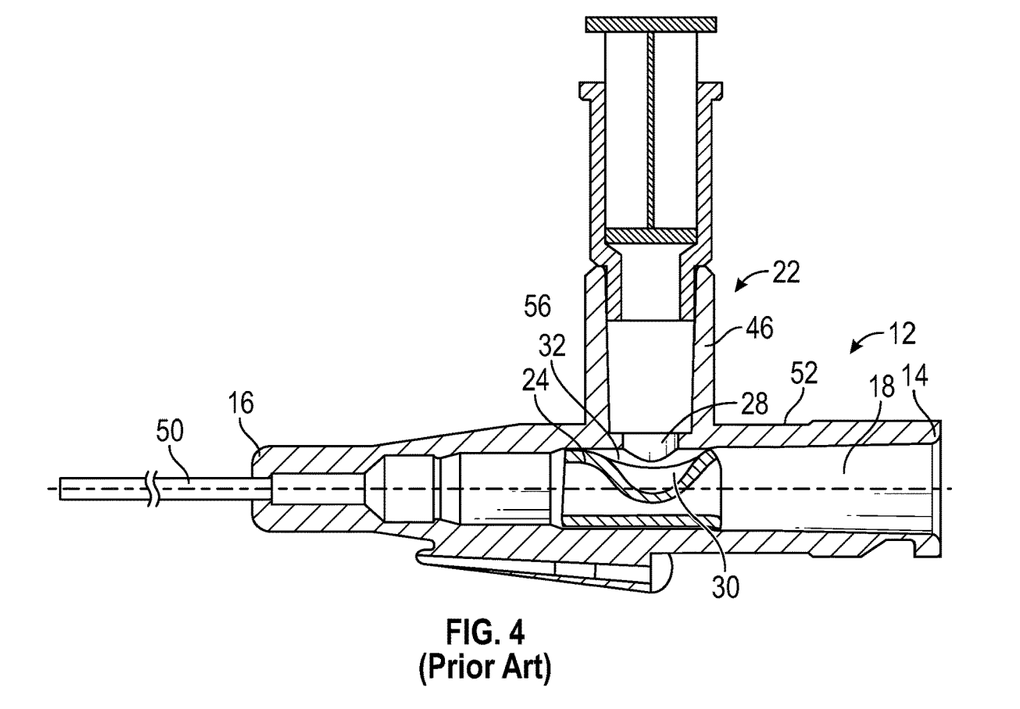
FIG. 4 is a cutaway view of a prior art catheter adapter, illustrating a gap in the elastomeric valve

Referring now to FIG. 4, deformation of the elastomeric port valve 24 in traditional devices is difficult to reliably control and may unseal the port opening 28, causing leakage of infusates or blood. Indeed, deformation of the elastomeric port valve 24 may change based on the relative position of the elastomeric port valve 24 and the port opening 28, as well as the injection speed of the fluid. It is thus not uncommon for a distal gap 32 to occur between the elastomeric port valve 24 and the catheter adapter 12 on the distal side of the catheter adapter 12. In some cases, deformation of the elastomeric port valve 24 forms both a proximal gap 30 and a distal gap 32, as shown in FIG. 4.

In some cases, injected fluid may flow out of the distal gap 32 because the fluid path is closed at the proximal end 14. This may lead to higher pressure on the proximal gap 30 side of the elastomeric port valve 24 during fluid injection. In other cases, the distal gap 32 may cause the elastomeric port valve 24 to be displaced proximally due to the force exerted on it by the exiting fluid. Such displacement may unseal the port opening 28, causing leakage of infusates or blood.

Figure 5:
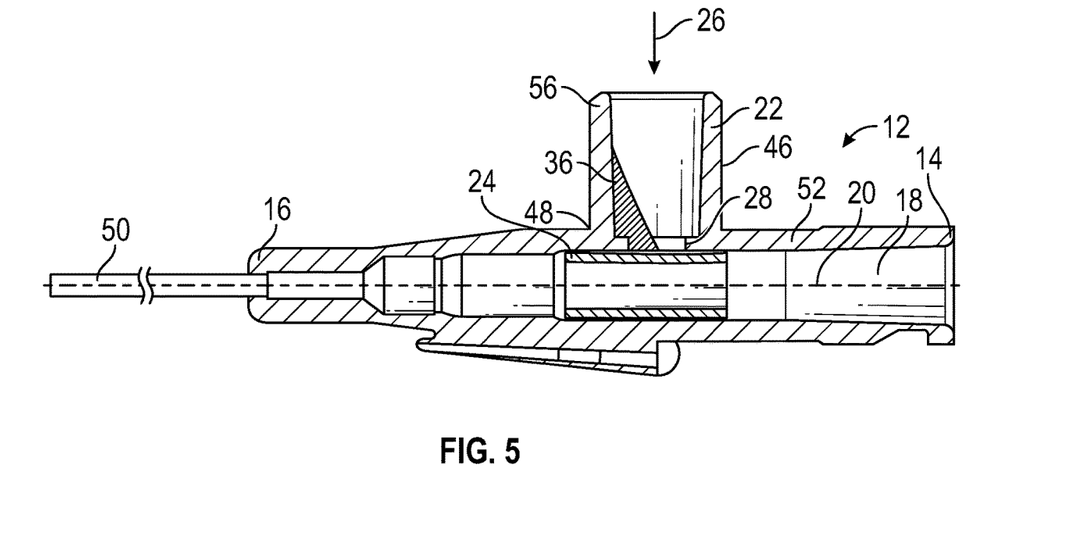
FIG. 5 is a cutaway view of an example vascular access device, according to some embodiments.

Referring now to FIG. 5, in some embodiments, the elastomeric port valve 24 may be disposed within the lumen 18 such that at least a portion of the elastomeric port valve 24 may occlude the port opening 28. In some embodiments, the port opening 28 may be disposed proximate to a proximal wall 46 of the side port 22. In some embodiments, the port opening 28 may be configured to couple to an infusion device, such as a syringe, to deliver the fluid to the fluid path. For example, in some embodiments, the syringe may be inserted into the side port 22. In some embodiments, the elastomeric port valve 24 may seal the port opening 28. Some embodiments of the syringe may apply the transverse force 26 to a top surface of the elastomeric port valve 24 to deform the elastomeric port valve 24 in a downward or transverse direction relative to the longitudinal axis 20. Some embodiments of the elastomeric port valve 24 may form a proximal gap 30 between the side port 22 and the lumen 18 in response to the transverse force 26, thereby opening a fluid path.

As mentioned previously, in some embodiments, the port opening 28 may include a structural geometry such as a sloped surface 36 configured to direct the fluid in the proximal direction as it enters the lumen 18 of the catheter adapter 12. As shown, in some embodiments, the sloped surface 36 may extend in the proximal direction from a distal wall 56 of the side port 22 to the port opening 28. Some embodiments of the sloped surface 36 may further extend in a diagonal or transverse direction from a location on the distal wall 56 elevated in a transverse direction relative to a location adjacent to the port opening 28. In some embodiments, the sloped surface 36 may extend from the distal wall 56 at an angle between about 30° and about 80°. In some embodiments, the sloped surface 36 may include a curve, a drop, or other suitable structural variation.

Figure 6:
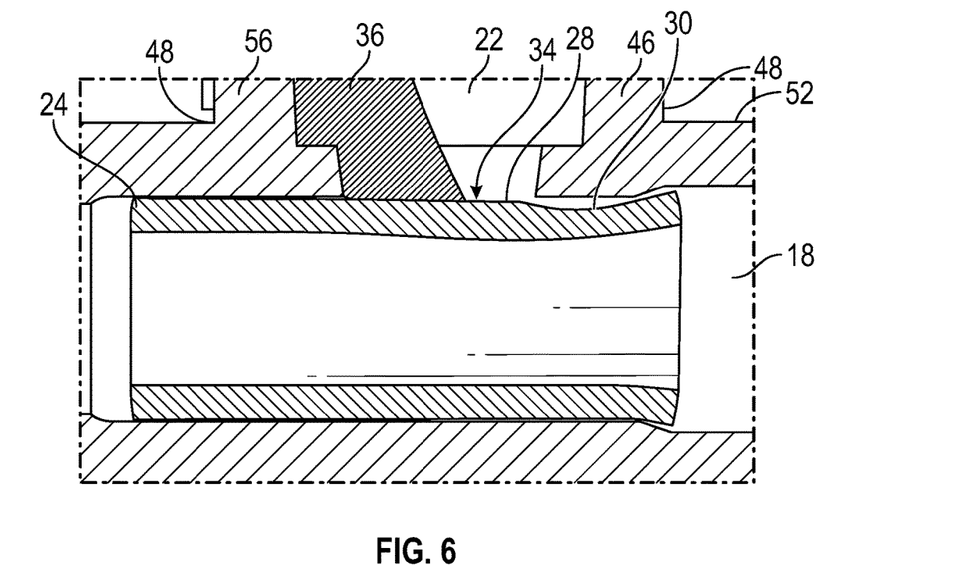
FIG. 6 is an enlarged cutaway view of the elastomeric valve disposed within the catheter adapter of FIG. 5.

Referring now to FIG. 6, in some embodiments, deforming the elastomeric port valve 24 may open a fluid path between the port opening 28 and the lumen 18. In some embodiments, this may form a proximal gap 30 between the elastomeric port valve 24 and the side port 22. In some embodiments, the proximal gap 30 may enable fluid to enter the catheter adapter 12 on the proximal side, or side near the opening 40 having a Luer adapter coupled thereto.

Figure 7:
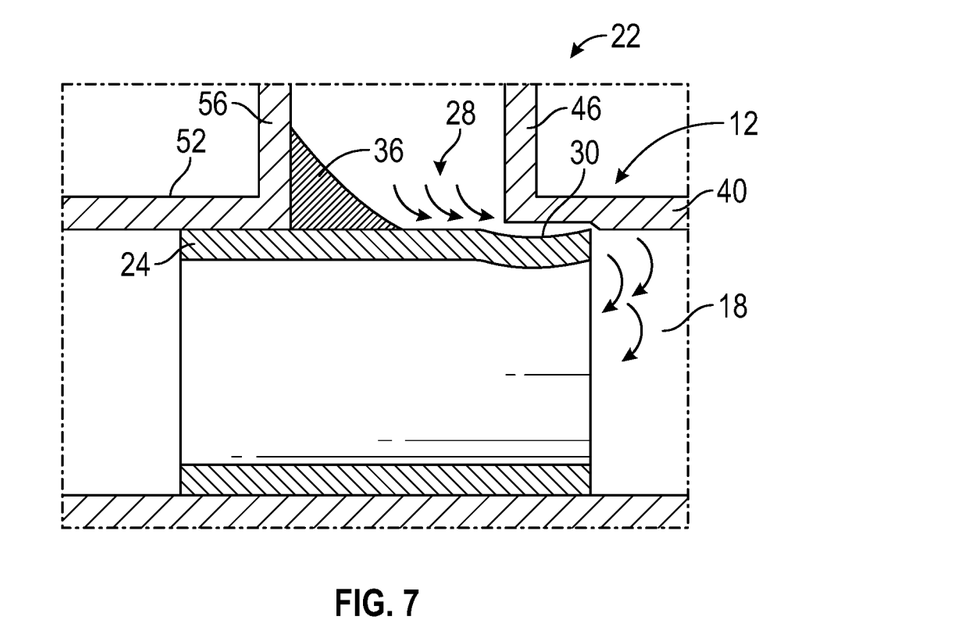
FIG. 7 is a cross-sectional view of the elastomeric valve and catheter adapter of FIG. 6, illustrating fluid flow in accordance with some embodiments.

Referring now to FIG. 7, some embodiments provide a structural port geometry to maximize the likelihood that injected fluid may exit the port opening 28 through the proximal gap 30. In some embodiments, the port opening 28 may be annular or may include any other suitable cross-sectional shape to create a fluid path from the side port 22 into the lumen 18 of the catheter adapter 12.

As previously discussed, in some embodiments, the syringe or other suitable infusion device may be inserted into the side port 22 to inject fluid and/or apply pressure to the elastomeric port valve 24, thereby forming a proximal gap 30 between the side port 22 and the elastomeric port valve 24. In this manner, some embodiments may create a fluid path from the side port 22 into the lumen 18 of the catheter adapter 12 via the proximal gap 30.

In some embodiments, as shown in FIG. 7, the side port 22 may extend in a substantially transverse direction relative to the longitudinal axis 20. In some embodiments, a distal wall 56 of the side port 22 may include a sloped surface 36 to direct fluid in a proximal direction as it flows from the side port 22 toward the elastomeric port valve 24 and into the lumen 18. In some embodiments, the fluid may then enter the lumen 18 through the proximal gap 30.

In some embodiments, the fluid may change course upon impinging the surface of the elastomeric port valve 24 through the proximal gap 30. In this manner, some embodiments of the fluid path may first flow through the proximal gap 30 in the proximal direction, and then change direction to flow through the elastomeric port valve 24 and lumen 18 in the distal direction.

Figure 8A:
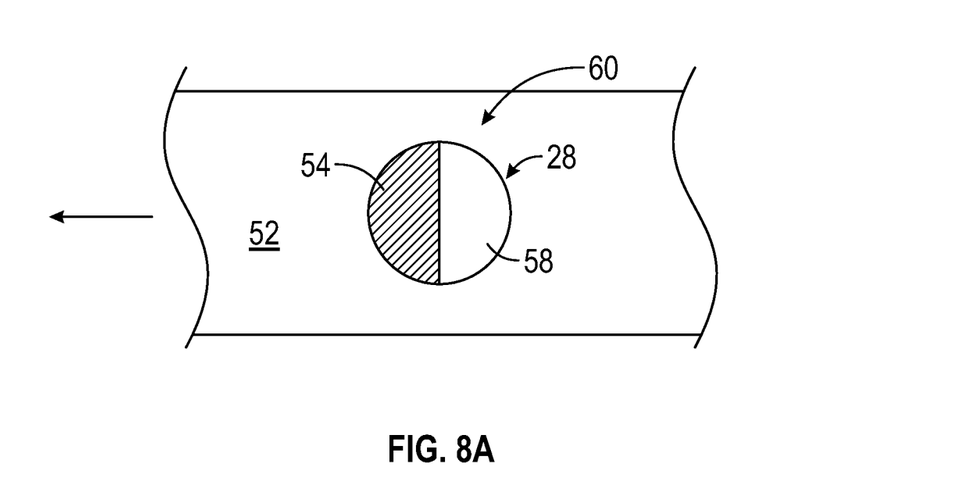
FIG. 8A is a top view of an example port opening having a half-circle structural geometry, according to some embodiments.
Figure 8B:
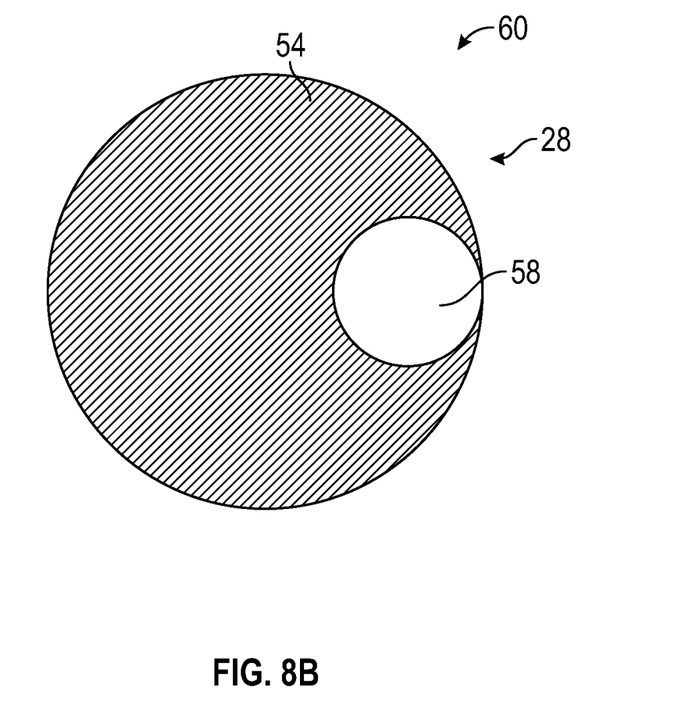
FIG. 8B is a top view of another example port opening having an off-center concentric circle structural geometry, according to some embodiments.
Figure 8C:
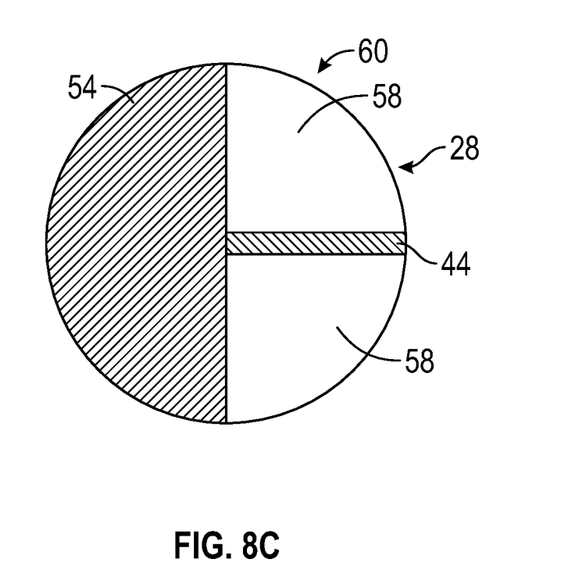
FIG. 8C is a top view of another example port opening having a rib integrated into a half-circle structural geometry, according to some embodiments.

Referring now to FIGS. 8A-8C, in some embodiments, the structural port geometry 34 may include a port opening 28 formed within a surface 52 of the catheter adapter 12 as a half circle, a pie shape, or any other suitable shape 60 configured to direct fluid from the side port 22 toward a proximal side of the port opening 28. In some embodiments, the port opening 28 may include a periphery smaller than a periphery of a distal end 48 of the side port 22. In this manner, in some embodiments, the port opening 28 may include a closed portion 54 and an open portion 58.

In these and other embodiments, the closed portion 54 of the shape 60 may be sloped in a downward or transverse direction toward the open portion 58 of the shape 60. The closed portion 54 of some embodiments may thus direct the fluid through the open portion 58 of the port opening 28. Accordingly, in some embodiments, the fluid may be directed to flow from the side port 22 into the lumen 18 of the catheter adapter 12 in the proximal direction.

Some embodiments may reduce the likelihood of high-volume flow in the distal direction, even in the event the distal gap 32 occurs. As discussed above, some embodiments may provide a sloped surface 36 or shape 60 sloped toward the proximal side of the port opening 28 to prevent formation of a distal gap 32 and thereby prevent displacement of the elastomeric port valve 24 within the lumen 18. In this manner, some embodiments may also improve elastomeric port valve 24 burst pressure and may reduce a likelihood of leakage of infusates and/or blood from the port opening 28.

In some embodiments, the port opening 28 may include a cross-sectional shape 60 having reduced dimensions relative to the distal end 48 of the side port 22. In some embodiments, the port opening 28 may include a circle having reduced dimensions and offset relative to the shape of the distal end 48. In these and other embodiments, one or more ribs 44 may extend at least partially across or along the port opening 28 to direct fluid toward the proximal side of the port opening 28. In some embodiments, the shape 60 and location of the port opening 28 relative to the distal end 48 of the side port 22 may direct fluid in the proximal direction such that the fluid enters the lumen 18 through the proximal gap 30.

In some embodiments, dimensions of the port opening 28 may be reduced significantly relative to the distal end 48 of the side port 22 without penalty to forces needed to inject the fluid through the fluid path. In some embodiments, the port opening 28 may be located near the proximal wall 46 of the side port 22 to increase the likelihood that fluid will enter the lumen 18 via the proximal gap 30. In some embodiments, this location of the port opening 28 may also decrease the likelihood of distal gap 32 formation.

Some embodiments of a method may provide a vascular access device 10. In some embodiments, the vascular access device 10 may include the catheter adapter 12 extending along the longitudinal axis 20. The catheter adapter 12 may include the proximal end 14, the distal end 16, and the lumen 18 extending therebetween. In some embodiments, the catheter may extend distally from the distal end 16 of the catheter adapter 12.

In these and other embodiments, the side port 22 may extend from the surface 52 of the catheter adapter 12 in a direction substantially transverse to the longitudinal axis 20. Some embodiments of the side port 22 may communicate with the lumen 18 through the port opening 28. In some embodiments, the port opening 28 may include a structural geometry configured to direct the fluid into the lumen 18 in the proximal direction. Some embodiments may further include an elastomeric port valve 24 disposed within the lumen 18 and sealing the port opening 28. In some embodiments, the elastomeric port valve 24 may be secured within the lumen 18 via friction, a press fit, an adhesive, or any other suitable method or device. In some embodiments, the elastomeric port valve 24 may be configured to deform in response to a force applied thereto.

Some embodiments of the method may further include activating the infusion device. In some embodiments, in response to activating the infusion device, a proximal end of the elastomeric port valve 24 may be deformed and a proximal gap 30 created between the proximal end of the elastomeric port valve 24 and an inner surface of the catheter adapter 12. In this manner, some embodiments may create a fluid path such that fluid flows proximally through the elastomeric port valve 24 and lumen 18.

In some embodiments, activating the infusion device may include applying a transverse force to the elastomeric port valve 24 via the infusion device to create the proximal gap 30. In some embodiments, coupling the infusion device to the side port 22 may include inserting a syringe 38 into the side port 22 such that a distal end of the syringe 38 contacts the port opening 28. In some embodiments, applying the transverse force may include depressing a plunger of the syringe 38 to deform the elastomeric port valve 24.

In some embodiments, activating the infusion device may include directing the fluid through the structural geometry of the port opening 28. Some embodiments of the structural geometry may include a half-circle shape, a pie shape, or a circle shape having a circumference smaller than the distal end of the side port. In some embodiments, activating the infusion device may include directing the fluid towards a rib 44 disposed across the port opening 28. Some embodiments of the rib 44 may include a contour to direct the fluid into the lumen 18 in the proximal direction.

In some embodiments, activating the infusion device may include directing the fluid towards the sloped surface 36. Some embodiments of the sloped surface 36 may extend in the transverse direction from a distal wall 56 of the side port 22 to the port opening 28. In some embodiments, the sloped surface 36 comprises an angle between about 30° and about 80°. In some embodiments, the sloped surface 36 may include a curve, a drop, or any other suitable structural feature to direct the fluid in the proximal direction through the port opening 28.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A vascular access device, comprising:
   a catheter adapter extending along a longitudinal axis and comprising a proximal end, a distal end, a lumen extending therebetween, and a side port disposed between the distal end of the catheter adapter and the proximal end of the catheter adapter, wherein the side port comprises a distal wall and a proximal wall opposite the distal wall;
   a port opening formed in a surface of the catheter adapter and in fluid communication with the side port of the catheter adapter and the lumen;
   a structural geometry to direct a fluid into the lumen in a proximal direction, wherein the structural geometry comprises a sloped surface forming a closed portion of the port opening, the sloped surface being sloped toward a proximal side of the port opening such that a thickness of a distal end of the structural geometry is greater than a thickness of a proximal end of the structural geometry, wherein the sloped surface extends in the proximal direction from the distal wall of the side port to form an open portion of the port opening in fluid communication with the lumen; and
   an elastomeric port valve disposed within the lumen and sealing the port opening, the elastomeric port valve configured to deform in response to a transverse force applied thereto such that a proximal gap is created between an inner wall forming the lumen and a proximal side of the elastomeric port valve, wherein the proximal gap opens a fluid path.

2. The vascular access device of claim 1, wherein the port opening is configured to couple to a syringe to deliver the fluid to the fluid path.

3. The vascular access device of claim 1, wherein the structural geometry comprises one of a half-circle shape and a pie shape.

4. The vascular access device of claim 1, wherein the structural geometry comprises a rib extending across at least a portion of the port opening to direct the fluid in the proximal direction through the port opening.

5. The vascular access device of claim 4, wherein the port opening comprises a periphery smaller than a periphery of a distal end of the side port such that the port opening comprises the closed portion and the open portion.

6. A vascular access device, comprising:
- a catheter adapter extending along a longitudinal axis and comprising a proximal end, a distal end, a lumen extending therebetween, and a side port disposed between the distal end of the catheter adapter and the proximal end of the catheter adapter, wherein the side port comprises a distal wall and a proximal wall opposite the distal wall;
- a port opening formed in a surface of the catheter adapter and in fluid communication with the side port of the catheter adapter and the lumen;
- a structural geometry to direct a fluid into the lumen in a proximal direction, wherein the structural geometry comprises a sloped surface extending in the proximal direction from the distal wall of the side port to the port opening to direct fluid through the port opening and into the lumen in the proximal direction, wherein a cross-section of the sloped surface comprises an arc shape extending from the distal wall, the sloped surface being sloped toward a proximal side of the port opening such that a thickness of a distal end of the structural geometry is greater than a thickness of a proximal end of the structural geometry; and
- an elastomeric port valve disposed within the lumen and sealing the port opening, the elastomeric port valve configured to deform in response to a transverse force applied thereto such that a proximal gap is created between an inner wall forming the lumen and a proximal side of the elastomeric port valve, wherein the proximal gap opens a fluid path.

7. A vascular access device, comprising:
- a catheter adapter extending along a longitudinal axis and comprising a proximal end, a distal end, a lumen extending therebetween, and a side port disposed between the distal end of the catheter adapter and the proximal end of the catheter adapter, wherein the side port comprises a distal wall and a proximal wall opposite the distal wall;
- a port opening formed in a surface of the catheter adapter and in fluid communication with the side port of the catheter adapter and the lumen;
- a structural geometry to direct a fluid into the lumen in a proximal direction, wherein the structural geometry comprises a sloped surface extending in the proximal direction from the distal wall of the side port to the port opening to direct fluid through the port opening and into the lumen in the proximal direction, wherein the sloped surface extends from the distal wall to an elastomeric port valve, the sloped surface being sloped toward a proximal side of the port opening such that a thickness of a distal end of the structural geometry is greater than a thickness of a proximal end of the structural geometry; and
- the elastomeric port valve disposed within the lumen and sealing the port opening, the elastomeric port valve configured to deform in response to a transverse force applied thereto such that a proximal gap is created between an inner wall forming the lumen and a proximal side of the elastomeric port valve, wherein the proximal gap opens a fluid path.

* * * * *